United States Patent
Feldman et al.

(10) Patent No.: US 10,758,176 B1
(45) Date of Patent: Sep. 1, 2020

(54) MEDICATION VENDING DEVICE THAT INTEGRATES WITH A MEDICAL DIAGNOSTICS DEVICE

(71) Applicant: Medherent, LLC, Annapolis, MD (US)

(72) Inventors: Joel F. Feldman, Owings Mills, MD (US); Yeardley W. Green, Stevenson, MD (US); Kimberly Langenhahn, Washington, DC (US)

(73) Assignee: Medherent, LLC, Annapolis, MD (US)

( * ) Notice: Subject to any disclaimer, the term of this patent is extended or adjusted under 35 U.S.C. 154(b) by 0 days.

(21) Appl. No.: 16/409,409

(22) Filed: May 10, 2019

(51) Int. Cl.
| | |
|---|---|
| G08B 7/00 | (2006.01) |
| A61B 5/00 | (2006.01) |
| A61J 7/04 | (2006.01) |
| A61J 7/00 | (2006.01) |
| G16H 20/13 | (2018.01) |
| A61B 5/11 | (2006.01) |

(52) U.S. Cl.
CPC .......... *A61B 5/4839* (2013.01); *A61B 5/742* (2013.01); *A61B 5/746* (2013.01); *A61J 7/0076* (2013.01); *A61J 7/0418* (2015.05); *A61J 7/0481* (2013.01); *G16H 20/13* (2018.01); *A61B 5/11* (2013.01); *A61J 2200/74* (2013.01)

(58) Field of Classification Search
CPC ....... A61B 5/4839; A61B 5/742; A61B 5/746; A61B 5/11; A61J 7/0418; A61J 7/0076; A61J 7/0481; A61J 2200/74; G16H 20/13
USPC ...................................................... 340/691.6
See application file for complete search history.

(56) References Cited

U.S. PATENT DOCUMENTS

| | | | |
|---|---|---|---|
| 5,036,462 A * | 7/1991 | Kaufman | A61J 7/0084 600/300 |
| 9,117,010 B2 | 8/2015 | Feldman et al. | |
| 9,477,817 B2 | 10/2016 | Feldman et al. | |
| 9,892,232 B2 | 2/2018 | Feldman et al. | |
| 2013/0211854 A1* | 8/2013 | Wagstaff | G06Q 10/10 705/2 |
| 2017/0262604 A1* | 9/2017 | Francois | G06Q 10/0631 |
| 2019/0133886 A1* | 5/2019 | Brecht | G16H 20/13 |

OTHER PUBLICATIONS

Product brochure for Carematix weight scale, Carematix, Inc., downloaded from web page: www.carematix.com/weight-scale.html <http://www.carematix.com/weight-scale.html>, download date: May 7, 2019; original posting date: unknown, 2 pages.

* cited by examiner

*Primary Examiner* — Naomi J Small
(74) *Attorney, Agent, or Firm* — Panitch Schwarze Belisario & Nadel LLP

(57) ABSTRACT

A medication vending device is provided that includes an input interface configured to receive a signal outputted by a medical diagnostics device which indicates a parameter of the patient's body, and a memory that stores a dosing schedule for medication loaded into the device. The medication vending device generates an electronic message whenever a vending event occurs. The dosing schedule is compared with the vending events, and a signal is outputted indicating when the medication is being properly vended in accordance with the dosing schedule, thereby indicating that the patient is adhering to the dosing schedule. An alert signal is generated when the patient is adhering to the dosing schedule, but the parameter is abnormal for the patient.

6 Claims, 9 Drawing Sheets

START

200 ~ Receive at a medication vending device a first signal outputted by a medical diagnostics device indicating a parameter of the patient's body

↓

202 ~ Generate an electronic message whenever a vending event occurs at the medication vending device

↓

204 ~ Electronically compare a dosing schedule with the vending events, and output a second signal indicating when the medication is being properly vended in accordance with the dosing schedule

↓

206 ~ Electronically compare the parameter received from the medical diagnostics device to a predefined parameter range that is designated as being normal for the patient, and output a third signal when the parameter is abnormal for the patient

↓

208 ~ Generate an alert signal when both the second signal and the third signal are outputted, thereby indicating that the patient is adhering to the dosing schedule, but that the parameter is abnormal for the patient

↓

END

Figure 2

High compliance

| Dosing Schedule | Actual time of vending event (blank box indicates no vended event was detected (i.e., dose was missed) | | | | | | |
|---|---|---|---|---|---|---|---|
| | Day 1 | Day 2 | Day 3 | Day 4 | Day 5 | Day 6 | Day 7 |
| 8:00 am | 805 am | 810 am | | 755 am | 801 am | 805 am | 745 am |
| 12:00 noon | 1145 am | 1201 pm | 1210 pm | 1205 pm | 1201 pm | 1201 pm | 1201 pm |
| 8:00 pm | 830 pm | 730 pm | 745 pm | 815 pm | 801 pm | 801 pm | 801 pm |

Figure 5A

Average degree of compliance

| Dosing Schedule | Actual time of vending event (blank box indicates no vended event was detected (i.e., dose was missed) | | | | | | |
|---|---|---|---|---|---|---|---|
| | Day 1 | Day 2 | Day 3 | Day 4 | Day 5 | Day 6 | Day 7 |
| 8:00 am | 801 am | 801 am | 805 am | 755 am | 801 am | 930 am | 755 am |
| 12:00 noon | 1201 am | | 1245 pm | 1210 pm | 1201 pm | 1201 pm | 1201 pm |
| 8:00 pm | 900 pm | 845 pm | 1045 pm | 1130 pm | 1130 pm | | 930 pm |

Figure 5B

Low degree of compliance

| Dosing Schedule | Actual time of vending event (blank box indicates no vended event was detected (i.e., dose was missed) | | | | | | |
|---|---|---|---|---|---|---|---|
| | Day 1 | Day 2 | Day 3 | Day 4 | Day 5 | Day 6 | Day 7 |
| 8:00 am | 801 am | | 805 am | 755 am | 801 am | 930 am | 755 am |
| 12:00 noon | 1156 am | 130 pm | 1156 am | 1230 pm | | 1201 pm | 1201 pm |
| 8:00 pm | 900 pm | 930 pm | 1105 pm | 1145 pm | 1030 pm | 1045 pm | 1055 pm |

Figure 5C

| Dosing Schedule | Actual time of vending event (blank box indicates no vended event was detected (i.e., dose was missed) | | | | | | |
|---|---|---|---|---|---|---|---|
| | Day 1 | Day 2 | Day 3 | Day 4 | Day 5 | Day 6 | Day 7 |
| 8:00 am | 805 am | 810 am | | 755 am | 800 am | 805 am | 730 am |
| 12:00 noon | 1230 pm | 1220 pm | 1230 pm | 1220 pm | 1230 pm | 1220 pm | 1225 pm |
| 8:00 pm | 1030 pm | 1020 pm | 1030 pm | 1030 pm | 1040 pm | | 1020 pm |

Figure 7

MEDICATION VENDING DEVICE THAT INTEGRATES WITH A MEDICAL DIAGNOSTICS DEVICE

CROSS-REFERENCE TO RELATED APPLICATIONS

This application is related to U.S. application Ser. No. 16/409,372 filed May 10, 2019 entitled "Medication vending device having adaptive alerts for the patient regarding when medication is scheduled to be taken in accordance with a dosing schedule"; and U.S. application Ser. No. 16/409,381 filed May 10, 2019 entitled "Medication vending device having an adaptive dosing schedule based on actual vending events."

BACKGROUND OF THE INVENTION

Medication vending devices are well-known in the art. See, for example, U.S. Pat. No. 9,117,010 (Feldman et al.), which is incorporated herein by reference in its entirety. One feature of such devices is that the devices and/or their related host site that maintains a patient-specific electronic medication administration record (eMAR)) may be programmed to generate alerts to patient caregivers (e.g., patient's medical care provider, family or friend) if any medications are not vended in accordance with a pre-programmed dosing schedule (also, referred to in the art as a "dosage schedule" or a "dose schedule").

Medical diagnostics devices exist today for measuring a large number of different parameters of the human body. These devices range from simple devices such as weight scales (e.g., parameter=weight) to complex blood sampling and analysis devices (e.g., parameter=white blood cell count). Many of these devices have "smart" capabilities, such as the ability to send alerts to pre-programmed entities when or if the measured parameters are outside of a predefined range.

The goal of most medication regimens is to maintain one or more parameters of the human body at a predefined level. Some of the parameters may be life-threatening if they divert significantly from the predefined level. The presumption is that adherence to a medication regimen by following the pre-programmed dosing schedule will maintain the parameter at the predefined level. This is why the alert feature of the medication vending device is important because an adherence failure may result in the parameter not being maintained at the predefined level.

However, in some instances, a medication is prescribed for a particular condition, but the medication, even when taken correctly, fails to address the condition, or after an initial period of success, the medication subsequently fails to address the condition. The alert feature of the medication vending device is not always useful in these instances, because no alert condition will be detected as long as the medication is being taken as directed.

A medication failure may be eventually detected when the patient visits a medical provider, but a significant period of time may elapse before such detection. However, the medical provider has no way to know for sure whether the medication failure was the result of non-adherence to a medication dosing schedule, or failure of the medication to perform as expected. This is because patients may either be untruthful about following the medication dosing schedule, or may not be able to respond with confidence as to whether they properly followed the medication dosing schedule, such as when the patient has cognitive impairment.

Accordingly, there is a need for more sophisticated functionality in a medication vending device and/or related system that can assist in detecting medication failures, even when a medication dosing schedule is being adhered to. The present invention fulfills such a need.

A medication vending device typically includes some form of alert each time that medication is scheduled to be taken in accordance with a dosing schedule that is set in the device. Typically, the alert is audible and/or visual. The alert is then turned off after a vending event is detected. For patients who are highly compliant with the dosing schedule after a lengthy period of time, the alert is not likely to be providing any useful assistance for the patient, and may be a source of annoyance, especially if the alert is audibly loud. For patients who have low (poor) compliance with the dosing schedule, the alert is very important, but since the alert is set for a typical patient, it may not be sufficient for the low compliance patient. Also, it may be necessary to provide alternative forms of alerts for such patients that are not provided at all for the normal patient. Notwithstanding these considerations, the common practice of medication vending devices is to provide only one default mode of alerts for all patients.

Accordingly, there is a need for more sophisticated functionality in a medication vending device and/or related system that can provide adaptive adherence intervention so that the alerts are modified based on actual degree of compliance data. The present invention fulfills such a need.

As discussed above, a medication vending device is pre-programmed with a dosing schedule. A sample dosing schedule is shown in FIG. 43 of U.S. Pat. No. 9,117,010. A patient's regular, daily sleep/wake cycle, or activity schedule may prevent the patient from strictly adhering to the dosing schedule. In such an instance, the patient will show low (poor) compliance with the dosing schedule. This may lead to generating a large number of alerts, which may trigger communications with a caregiver regarding the low compliance. However, if the low compliance is due to the patient's regular, daily sleep/wake cycle, or activity schedule, the patient will not be able to improve their compliance level.

Accordingly, there is a need for providing an adaptive dosing schedule that would permit predefined variations to be made to the dosing schedule when low compliance issues arise. The present invention fulfills this need.

SUMMARY OF THE PRESENT INVENTION

A medication vending device is provided that includes an input interface configured to receive a first signal outputted by a medical diagnostics device which indicates a parameter of the patient's body, and a memory that stores a dosing schedule for medication loaded into the device, and a predefined parameter range for the parameter received from the medical diagnostics device that is designated as being normal for the patient, wherein a parameter that is outside of the predefined range is designated as being abnormal for the patient. The medication vending device generates an electronic message whenever a vending event occurs. The dosing schedule is compared with the vending events, and a second signal is outputted indicating when the medication is being properly vended in accordance with the dosing schedule, thereby indicating that the patient is adhering to the dosing schedule. The parameter received from the medical diagnostics device is compared to the predefined parameter range, and a third signal is outputted when the parameter is abnormal for the patient. An alert signal is generated when the controller outputs both the second signal and the third signal, thereby indicating that the patient is adhering to the dosing schedule, but that the parameter is abnormal for the patient.

BRIEF DESCRIPTION OF THE DRAWINGS

Preferred embodiments of the present invention will now be described by way of example with reference to the accompanying drawings:

FIG. 2 is a flowchart for implementing the system of FIG. 1.

FIGS. 5A-5C show vending event data for the system of FIG. 3.

FIG. 7 shows vending event data for the system of FIG. 6.

DETAILED DESCRIPTION OF THE INVENTION

Certain terminology is used herein for convenience only and is not to be taken as a limitation on the present invention.

The words "a" and "an", as used in the claims and in the corresponding portions of the specification, mean "at least one."

I. Definitions

The following definitions are provided to promote understanding of the present invention.

degree of compliance—This is a measurement that factors in at least one or both of the following parameters:
  i. percentage of doses in a predefined sampling period that are vended within a predefined time window of the dosing schedule time, and
  ii. percentage of doses in a predefined sampling period that are not vended (i.e., missed doses).

The degree of compliance may have various levels of granularity, such as two levels (i.e., compliant or non-compliant), or three levels (i.e., high degree, average degree, low degree).

Other factors may also be included, such as double-dosing.

high degree of compliance—This is a measurement that factors in one or both of the following parameters:
  i. percentage of doses in a predefined sampling period that are vended within a predefined time window of the dosing schedule time being equal to or greater than a first predefined value, and ii. percentage of doses in a predefined sampling period that are not vended (i.e., missed doses) being less than a second predefined value low degree of compliance—This is a measurement that factors in one or both of the following parameters:
  i. percentage of doses in a predefined sampling period that are vended within a predefined time window of the dosing schedule time being less than a third predefined value, and
  ii. percentage of doses in a predefined sampling period that are not vended (i.e., missed doses) being equal to or greater than a fourth predefined value.

average degree of compliance—This is a degree of compliance that falls between a high and low degree of compliance, and thus its exact values are determined by the values of the high and low degrees of compliance. If there are only two degrees of compliance (compliant or non-compliant), there would be no average degree of compliance.

II. Detailed Description

A. Medication Vending Device Used with Medical Diagnostics Device

Figure 1:
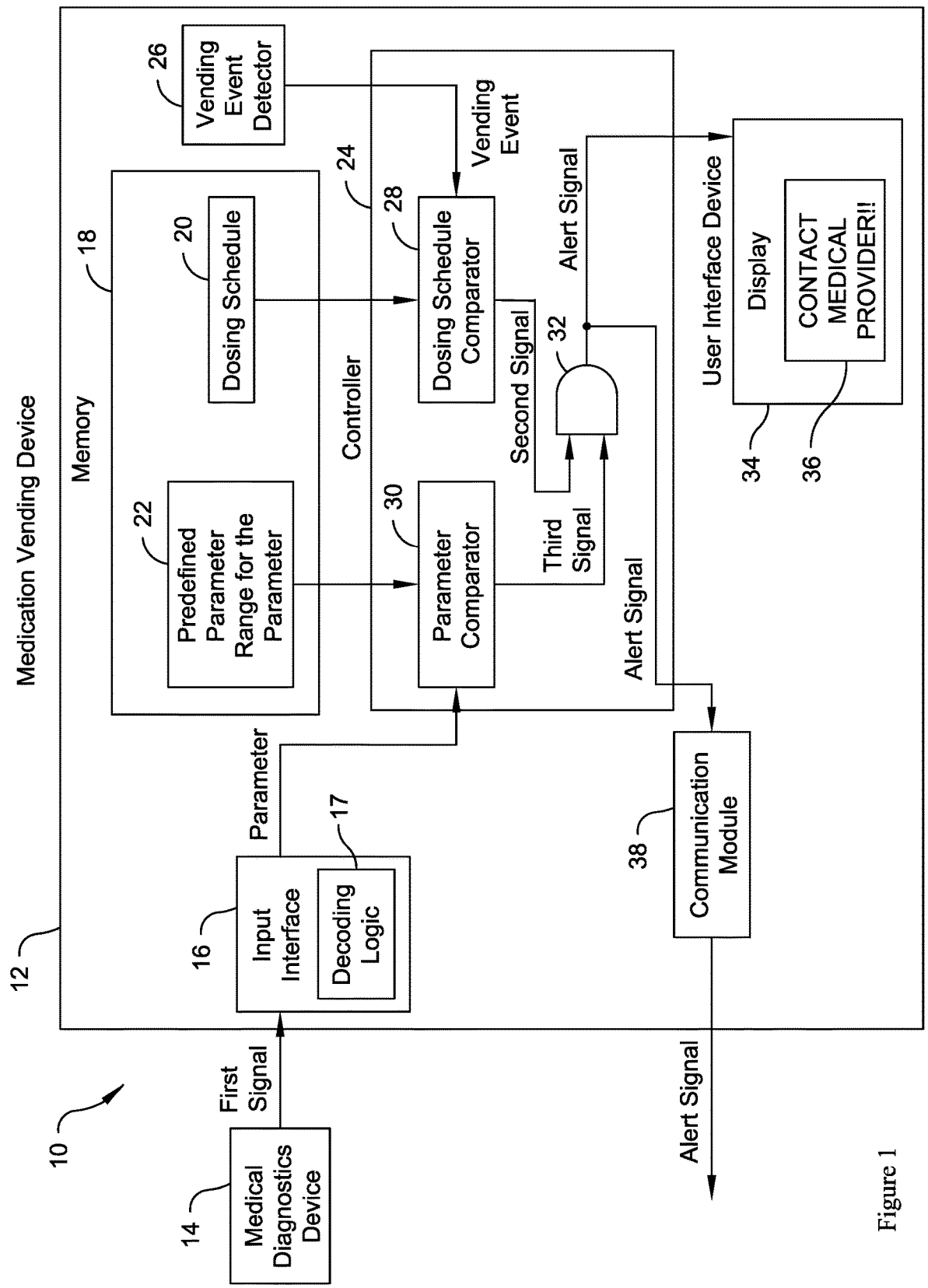
FIG. 1 is a schematic diagram of a system that integrates a medication vending device with a medical diagnostics device in accordance with one preferred embodiment of the present invention.

FIG. 1 is a schematic diagram of a system 10 that integrates a medication vending device 12 with a medical diagnostics device 14 in accordance with one preferred embodiment of the present invention. One example of the medication vending device 12 may be the device described in U.S. Pat. No. 9,117,010, enhanced with the features described below. Examples of the medical diagnostics device 14 include a weight scale and a movement sensor. A weight scale may be useful for detecting congestive heart failure (CHF) or preeclampsia (high blood pressure during pregnancy) because sudden weight gain caused by either of these conditions can indicate a potential need for hospitalization. One suitable weight scale that may be integrated with the medication vending device 12 is commercially available from Carematix, Inc. A movement sensor, such as a FitBit® may also be integrated with the medication vending device 12. The medical diagnostics device 14 may also be a more complex device, such as a home-based blood sampling and analysis device that detects blood cell counts or glucose levels. The medical diagnostics device 14 outputs a first signal that includes information regarding a parameter of the patient's body.

In one preferred embodiment, the first signal is communicated to the medication vending device 12 via Bluetooth® and the information regarding the parameter of the patient's body is encoded in the Bluetooth signal. In another preferred embodiment, the first signal is communicated to the medication vending device 12 via a wireless network within a patient's home. Alternatively, wired communication may be used, such as via a USB port. While FIG. 1 shows only one medical diagnostics device 14, a plurality of such devices may communicate with the medication vending device 12.

The medication vending device includes an input interface 16 for receiving the first signal from the medical diagnostics device 14. The input interface 16 is pre-programmed with suitable decoding logic 17 to allow for extraction of the parameter of the patient's body (e.g., weight, steps taken in past 24 hours, blood level) from the first signal.

The medication vending device 12 further includes memory 18 that stores a dosing schedule 20 for medication loaded into the medication vending device 12, and a predefined parameter range 22 for the parameter received from the medical diagnostics device 14 that is designated as being normal. By definition, a parameter that is outside of the predefined range is designated as being abnormal.

The medication vending device further includes a controller 24 configured to perform the following functions:

i. Generate an electronic message whenever a vending event occurs at the medication vending device 12. The medication vending device 12 includes a vending event detector 24 that detects such an event when medication is released from the medication vending device 12.

ii. Electronically compare the dosing schedule 20 with the vending events in a dosing schedule comparator 28 which outputs a second signal indicating when the medication is being properly vended in accordance with the dosing schedule, thereby indicating that the patient is adhering to the dosing schedule. Medication vending devices, such as the device described in U.S. Pat. No. 9,117,010, may be configured to output a signal when medication is not being properly vended in accordance with the dosing schedule, thereby indicating that the patient is not adhering to the dosing schedule. The medication vending device 12 may also provide this functionality since non-compliance may require intervention. However, the preferred embodiment of the present invention is directed to the condition wherein the patient is adhering to the dosing schedule.

iii. Electronically compare the parameter received from the medical diagnostics device 14 (as outputted by the input interface 16) to the predefined parameter range in parameter comparator 30, and output a third signal when the parameter is abnormal.

iv. Generate an alert signal when the controller 24 outputs both the second signal and the third signal, thereby indicating that the patient is adhering to the dosing schedule, but that the parameter is abnormal. This condition is depicted by AND gate 32, but is preferably coded in software within the controller 24.

The medication vending device 12 further includes a user interface device 34 having display 36. The controller 24 is further configured to display the alert signal on the display 36 to inform the patient to contact a medical provider regarding the abnormal parameter. The medication vending device 12 further includes a communication module 38 configured to communicate electronic messages from the medication vending device 12 to an external location. The user interface device 34 may also include audible alert information in addition to, or instead of, displayed information. The controller 24 is further configured to electronically communicate the alert signal to the external location via the communication module 38. The external location may be a medical provider, family member, or the like. Again, the alert signal indicates the presence of the abnormal parameter.

As discussed above in the background section, the conventional alert feature of a medication vending device provides an alert condition only when there is an adherence failure (i.e., medication is not being taken as directed). However, in some instances, a medication is prescribed for a particular condition, but the medication, even when taken correctly, fails to address the condition, or after an initial period of success, the medication subsequently fails to address the condition. The conventional alert feature of the medication vending device is not always useful in these instances, because no alert condition will be detected as long as the medication is being taken as directed.

The new type of alert signal described above addresses this deficiency. In addition, it provides valuable information to a medical provider, namely by communicating to the medical provider that the abnormal parameter was not the result of non-adherence to a medication dosing schedule. The medical provider may then focus their attention on other potential causes of the abnormal parameter, such as failure of the medication to perform as expected, or deterioration of the patient's condition.

FIG. 2 is a flowchart for implementing the system 10 of FIG. 1 and includes the following steps.

STEP 200: Receive at a medication vending device 12 a first signal outputted by a medical diagnostics device 14 indicating a parameter of the patient's body.

STEP 202: Generate an electronic message whenever a vending event occurs at the medication vending device 12.

STEP 204: Electronically compare a dosing schedule with the vending events, and output a second signal indicating when the medication is being properly vended in accordance with the dosing schedule.

STEP 206: Electronically compare the parameter received from the medical diagnostics device to a predefined parameter range that is designated as being normal, and output a third signal when the parameter is abnormal.

STEP 208: Generate an alert signal when both the second signal and the third signal are outputted, thereby indicating that the patient is adhering to the dosing schedule, but that the parameter is abnormal.

EXAMPLE

Patient's medication prescription: 10 mg of lisinopril (for CHF)
Dosing schedule: "1" 10 mg tablet per day. Take same time every day. No double dose if daily dose is missed.
Medical diagnostics device: Weight scale
Patient's current weight: 160 lbs
Predefined parameter range: 130-170 lbs When tracking patient adherence to the dosing schedule, the dosing schedule comparator 28 is programmed with rules to determine whether a patient is adhering to the dosing schedule (compliance=Y), or is not adhering to the dosing schedule (compliance=N). Certain deviations may be allowed so that failure to strictly comply is not flagged as non-compliance. For example, a rule may be set that one missed dose, or one instance of double-dosing (assuming that the medication vending device 12 allows for double-dosing—default setting does not allow for double-dosing), per 14 day period is still in compliance. Likewise, a 6 hour time window may be set for when the patient should take the medication every day to comply with the dosing schedule to take the medication at the same time every day. If the patient takes the medication between 6:00 am and 12:00 noon every day, as determined by the vending event detector 26, one daily dose taken before 6:00 am or after 12:00 noon per 14 day period is still in compliance of the dosing schedule to take the medication at the same time every day.

In this example, the primary concern is weight gain due to fluid build-up, so any weight gain of more than 10 lbs is cause for immediate concern, whereas weight loss up to 30 lbs is not a significant medical concern for this patient who may be overweight to begin with. Allowable deviations may also be set for the predefined parameter range. For example, a rule may require a patient to be over 170 lbs for three consecutive days before the patient is considered to be out of the predefined parameter range. However, the 170 lb value may be strictly enforced as the upper limit if the patient's weight gain from 160 lbs to 171 lbs is rapid (e.g., occurs in less than x number of days).

In operation, as long as compliance=Y, the controller 24 continuously checks for an out-of-range value for the parameter (here, weight), and outputs an alert signal if the parameter is out-of-range. If compliance=N, the medication vending device 12 may be programmed to take other sorts of actions, similar to those described in U.S. Pat. No. 9,117,010, whether or not the patient's parameter is within the predefined parameter range.

B. Medication Vending Device Having Adaptive Adherence Alerts

Figure 3:
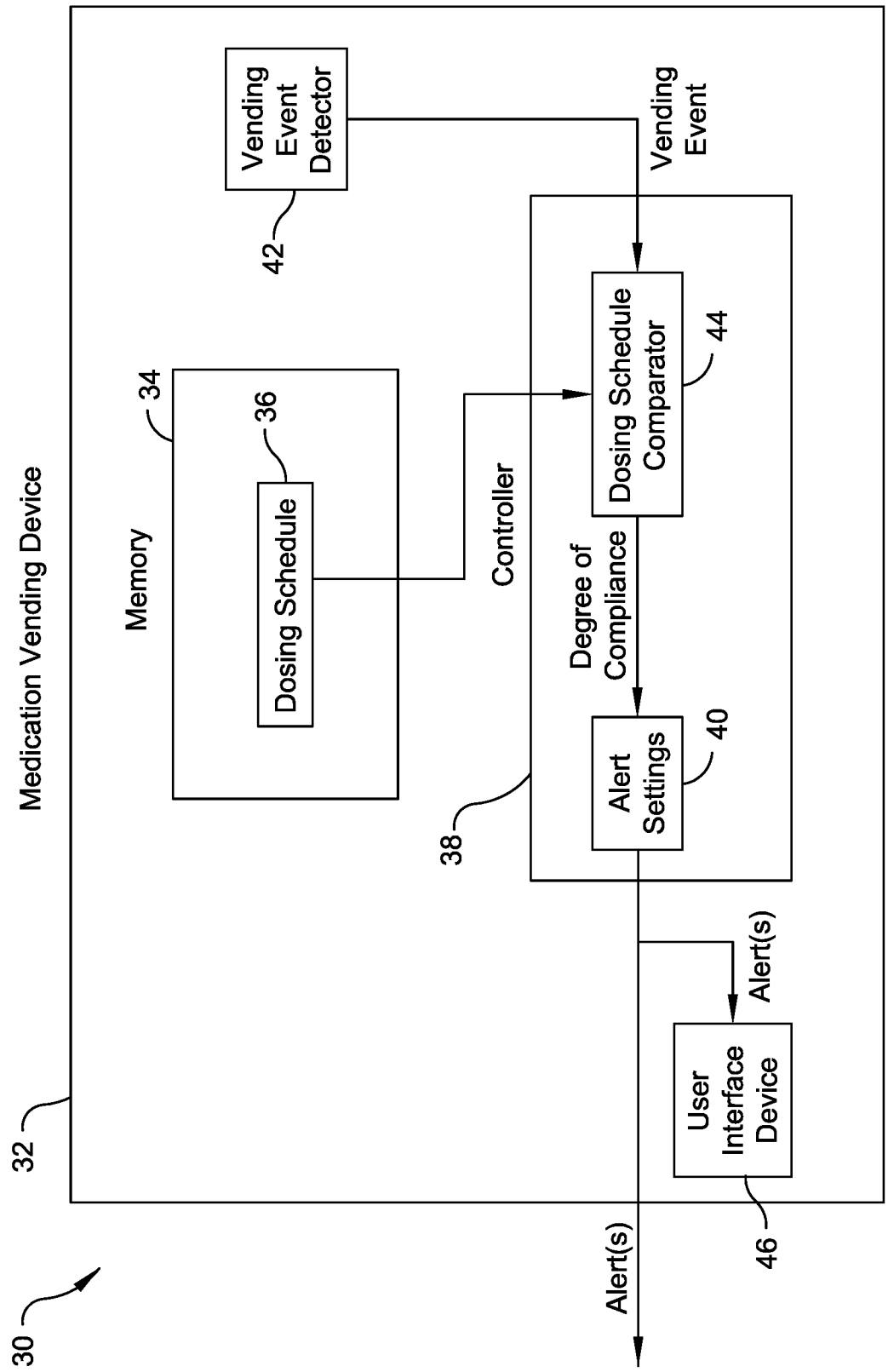
FIG. 3 is a schematic diagram of a system that provides adaptive alerts for a medication vending device in accordance with another preferred embodiment of the present invention.

FIG. 3 is a schematic diagram of a system 30 that provides adaptive adherence alerts for a medication vending device 32 in accordance with one preferred embodiment of the present invention. One example of the medication vending device 32 may be the device described in U.S. Pat. No. 9,117,010, enhanced with the features described below.

The medication vending device 32 includes memory 34 that stores a dosing schedule 36 for medication loaded into the medical vending device 32. The medication vending device 32 also includes a vending event detector 38 that outputs a vending event signal when medication is released from the medication vending device 32.

The fact that a medication is vended does not ensure that the patient actually took the medication. However, in the preferred embodiment, it is presumed that a vended medication is actually taken by the patient. The time of vending is also presumed to be the scheduled time for the patient to take the vended medication.

The medication vending device 32 further includes a controller 38 configured to perform the following functions:

i. Generate one or more alerts for the patient when medication is scheduled to be vended in accordance with the dosing schedule 36. The alerts are stored in alert settings 40. The alerts may include sound, light, phone calls, and mobile device messaging.

ii. Generate an electronic message whenever a vending event occurs at the medication vending device 32. The medication vending device 32 includes a vending event detector 42 that detects such events.

iii. Periodically compare the dosing schedule 36 with the vending events in dosing schedule comparator 44, and output a signal indicating a degree of compliance with the dosing schedule 36, and iv. Periodically modify the one or more alerts based on the degree of compliance with the dosing schedule 36, wherein a high degree of compliance with the dosing schedule 36 results in reducing the level of the one or more alerts, and a low degree of compliance with the dosing schedule 36 results in increasing the level of the one or more alerts. The alert modifications are made via changes to the alert settings 40.

In one embodiment, the one or more alerts have a default setting, and the default setting is modified based on the periodically determined degree of compliance. The default setting may also be used as the initial setting when the medication vending device 32 is placed into use.

In one embodiment, the one or more alerts have on and off settings. In this embodiment, a high degree of compliance with the dosing schedule 36 results in turning off or reducing the frequency of one or more of the alerts, and a low degree of compliance with the dosing schedule 36 results in turning on or increasing the frequency of one or more of the alerts. For example, the initial alerts may be only audiovisual which are communicated via a display and/or speaker of user interface device 46 of the medication vending device 32. If a patient has been detected as having poor compliance, an additional type of alert, such as a text message, may be added to the alert settings.

If the dosing schedule 36 includes multiple dosing times per day, the degree of compliance is measured for each of the dosing times. The periodic modifications of the one or more alerts may occur separately for each of the dosing times.

Figure 4:
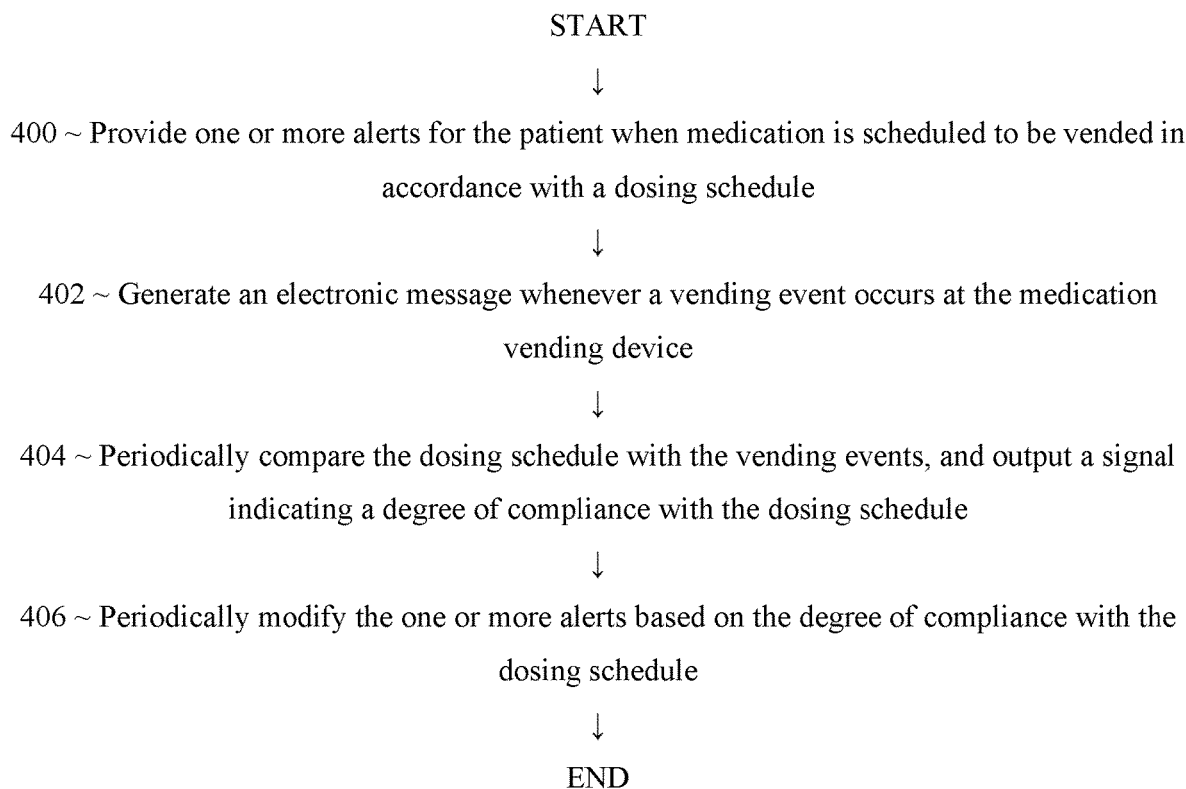
FIG. 4 is a flowchart for implementing the system of FIG. 3.

FIG. 4 is a flowchart for implementing the system 10 of FIG. 1 and includes the following steps.

STEP 400: Provide one or more alerts for the patient when medication is scheduled to be vended in accordance with a dosing schedule.

STEP 402: Generate an electronic message whenever a vending event occurs at the medication vending device.

STEP 404: Periodically compare the dosing schedule with the vending events, and output a signal indicating a degree of compliance with the dosing schedule.

STEP 406: Periodically modify the one or more alerts based on the degree of compliance with the dosing schedule, wherein a high degree of compliance with the dosing schedule results in reducing the level of the one or more alerts, and a low degree of compliance with the dosing schedule results in increasing the level of the one or more alerts.

The degree of compliance may be measured in many different ways. In one preferred embodiment, the degree of compliance is measured as follows:

1. Calculate the percentage of doses during a predefined sampling period (e.g., 30 days) that were vended within a predefined time window of the dosing schedule time, such as ±2 hours.

2. Set a range for different degrees of compliance. Example:

High degree of compliance=90-100% of doses were vended within the predefined time window of the dosing schedule time.

Average degree of compliance=70-89% of doses were vended within the predefined time window of the dosing schedule time.

Low degree of compliance=Less than 70% of doses were vended within the predefined time window of the dosing schedule time.

The degree of compliance may have more levels of granularity than high, medium, and low.

A missed dose may be counted as a dose that was not vended within the predefined time window of the dosing schedule time. Alternatively, if a missed dose is a very serious concern for a particular medicine, or for a particular patient, the rules for calculating high, average, and low degree of compliance can treat a missed dose as a separate rule. For example, a high degree of compliance may require no missed doses within the last sampling period, even if 90-100% of vended doses were vended within the predefined time window of the dosing schedule time. Likewise, a low degree of compliance may exist if there was a single missed dose within the last sampling period, even if 70% or more of doses were vended within the predefined time window of the dosing schedule time.

The alerts in the alert settings 40 preferably have a default setting which is then modified based on a periodically determined level of compliance. In one example, the default setting is not changed if the patient is achieving only an average degree of compliance. However, if the patient exhibits a high or low degree of compliance, the default setting is changed to whatever new alert settings are designated as representing a high or low degree of compliance. Likewise, if the degree of compliance changes from high to average, or from low to average, during a subsequent sampling period, then the default setting is restored.

In another preferred embodiment, the alert settings have only two different settings, one indicating compliance, and another indicating non-compliance. For example, compliance may be defined as 85% or more of doses being vended within the predefined time window of the dosing schedule time, and non-compliance may be defined as less than 85% of the doses being vended within the predefined time window of the dosing schedule time.

Example

Dosing schedule: Patient's dosing schedule is similar to the dose schedule shown for Patient ID 1234 in FIG. 43 of U.S. Pat. No. 9,117,010, repeated below for convenience.

TABLE 1

| Dosing schedule | Dispensedmeds (meds that are scheduled to be dispensed and which were previously placed in the vending machine) |
|---|---|
| 8:00 am | 1 pill of MEDICINE A |
| | 1 pill of MEDICINE B |
| | 2 pills of MEDICINE C |
| 12:00 noon | 1 pill of MEDICINE D |
| | 1 pill of MEDICINE E |
| 8:00 pm | 1 pill of MEDICINE A |
| | 1 pill of MEDICINE B |
| | 2 pills of MEDICINE C |

In this example, the medications are vended in multi-unit dose packages (MUDPs). Thus, a single package contains all of the medications vended at a respective dose time. This example relates to MUDPs, but the scope of the present invention includes single non-packaged medicines, or packages that include only one medicine type per package.

In FIG. 43 of U.S. Pat. No. 9,117,010, the time of the prompts is set to always equal the dose schedule times, and there is only one prompt for each dose time. However, in the present invention, these prompts are not rigidly fixed, and may even be turned off. Likewise, additional types of prompts may be set for each dose time depending upon the degree of compliance.
Predefined Time Window of the Dosing Schedule Time
±2 hours
Missed Dose
Treat as dose not vended within the predefined time window of the dosing schedule time.

In this Example, the medication vending device allows for vending to occur outside of the ±2 hour predefined time window of the dosing schedule time. However, in one preferred embodiment, no vending is permitted outside of this time window. In such an embodiment, the doses that were vended outside of the two hour window in this Example would be treated as missed doses, since vending would not be possible. This is the same result as shown in this Example, since it treats a dose not vended within the predefined time window of the dosing schedule time as a "Missed dose."
Degree of Compliance Rules
High degree of compliance=90-100% of doses were vended within the predefined time window of the dosing schedule time.
Average degree of compliance=70-89% of doses were vended within the predefined time window of the dosing schedule time.
Low degree of compliance=Less than 70% of doses were vended within the predefined time window of the dosing schedule time.
Current Alert Settings
Default setting
Sampling Period
7 days (The sampling period would preferably be longer than 7 days, but for ease of illustration, a relatively short sampling period is used.)
Alert Settings
Default setting (used when there is an average degree of compliance, and also used as the initial setting): 5 minutes prior to dosing schedule time, display "TAKE [time x] MEDS" on display of user interface device 46, and sound a 5 second alert signal. Sound a 15 second alert signal at dosing schedule time, and 5 minutes after dosing schedule time, if dose has not yet been vended. Delete "TAKE [time x] MEDS" on the display after dose has been vended, or 2 hours after dosing schedule time if dose has not yet been vended. (In this example, [time x] would be either "8:00 am" or "12:00 noon" or "8:00 pm.")
High degree of compliance setting: At dosing schedule time, display "TAKE [time x] MEDS" on display of user interface device 46, and sound a 5 second alert signal. Delete "TAKE [time x] MEDS" on the display after dose has been vended, or 2 hours after dosing schedule time if dose has not yet been vended.
Low degree of compliance setting: 1 hour prior to dosing schedule time, display "TAKE [time x] MEDS IN [x minutes]" on display of user interface device 46, and sound a 5 second alert signal. Sound a 15 second alert signal at dosing schedule time, and every 15 minutes after dosing schedule time for 2 hours after the dosing schedule time, if dose has not yet been vended. Delete "TAKE [time x] MEDS" on the display after dose has been vended, or 2 hours after dosing schedule time if dose has not yet been vended. Send text alert to patient's mobile device 5 minutes before each dosing schedule time.

Here, the "x minutes" is a countdown timer, starting at 60 minutes and decrementing each minute. At the dosing schedule time, "x minutes" is replaced by the word "NOW," and display continues to show the message "TAKE [time x] MEDS NOW" until the dose has been vended, or until 2 hours after the dosing schedule time if the dose has not yet been vended.
Alert Settings Granularity
Same alert setting for all dosing times.

FIG. 5A shows a 7 day sampling period of vending events. The degree of compliance is 95% (20/21) which meets the criteria for a high degree of compliance. All vended doses were vended within two hours of the dosing schedule time. One dose was missed (Day 3 8:00 am dose). Accordingly, the alert settings are changed from the default setting (which may have been the initial setting) to the high degree of compliance setting.

FIG. 5B shows a subsequent 7 day sampling period of vending events for the same patient's device. The degree of compliance is 76% (16/21). That is, only 16 of the 21 doses were vended in compliance with the dosing schedule time. Two doses were completely missed, and three doses were vended late (i.e., more than two hours after the dosing schedule time). Accordingly, the alert settings are changed from the high degree of compliance setting back to the default setting.

FIG. 5C shows another subsequent 7 day sampling period of vending events for the same patient's device. The degree of compliance is 67% (14/21). That is, only 14 of the 21 doses were vended in compliance with the dosing schedule time. Two doses were completely missed, and five doses were vended late (i.e., more than two hours after the dosing schedule time). Accordingly, the alert settings are changed from the default setting to the low degree of compliance setting. Thus, in addition to more frequent audiovisual alerts, the patient now receives text alerts to their mobile device 5 minutes before each dosing schedule time.

In this example, the alert setting granularity is set to apply the same alert setting for all dosing times. Accordingly, a single degree of compliance is calculated based on all of the dosing schedule times in the sampling period. However, in an alternative embodiment, the degree of compliance is individually measured for each dosing time, and the alert settings are customized by dosing time.

Consider, for example, the sampling period shown in FIG. 5B. Here, the patient exhibits a high degree of compliance (7/7=100%) for the 8:00 am dosing time, an average degree of compliance (6/7=86%) for the 12:00 noon dosing time, and a low degree of compliance (3/7=43%) for the 8:00 pm dosing time. Accordingly, the alert settings may be set as follows:

8:00 am dosing time: high degree of compliance setting
12:00 noon dosing time: default setting
8:00 pm dosing time: low degree of compliance setting In this manner, the patient is not subjected to extra alerts for highly compliant dosing times, but receives the extra alerts for the low compliant dosing times. This customization may reduce "alert fatigue" wherein a patient may tend to start ignoring all alerts if many of the alerts provide unnecessary reminders.

The examples shown in FIGS. 5A-5C calculate the degree of compliance using the percentage of doses that were vended within a predefined time window of the dosing schedule time, and wherein a missed dose is considered only as a failure to vend within the predefined time window. However, for certain medications, even though the patient is provided with a dosing schedule, the more critical factor may be whether the medication was taken at all, and not necessarily when it was taken. For these medications, it may be desirable to focus more on missed doses, as opposed to time frames of vended (taken) doses. FIG. 5A shows one missed dose, and FIGS. 5B and 5C show two missed doses. Consider the following alternative compliance rules for a sampling period:

High degree of compliance=90-100% of doses were vended (i.e., not missed, and presumed to be taken).
Average degree of compliance=70-89% of doses were vended (i.e., not missed, and presumed to be taken).
Low degree of compliance=Less than 70% of doses were vended (i.e., missed, and presumed not to be taken).

Under these alternative compliance rules, the overall degree of compliance in FIG. 5A is 95% (20/21); and in FIGS. 5B and 5C is 90% (19/21), meaning that the patient is in high compliance for all sampling periods. However, if the degree of compliance is measured by individual dosing schedule times, then the patient has a high degree of compliance (100% 7/7) for only some of the dosing schedule times, and has an average degree of compliance for other dosing schedule times (86% 6/7). These percentages may then be used to determine the appropriate alert settings in the same manner as described above.

In a more complex scenario, the degree of compliance may factor in both the percentage of doses in a predefined sampling period that are vended within a predefined time window of the dosing schedule time, and the percentage of doses in a predefined sampling period that are not vended (i.e., missed doses). For example, each of these factors may be given a weighting, wherein the weighting depends upon the relative importance of taking the specific medication on time compared to the importance of not missing any doses.

C. Medication Vending Device Having Adaptive Dosing Schedule

Figure 6:
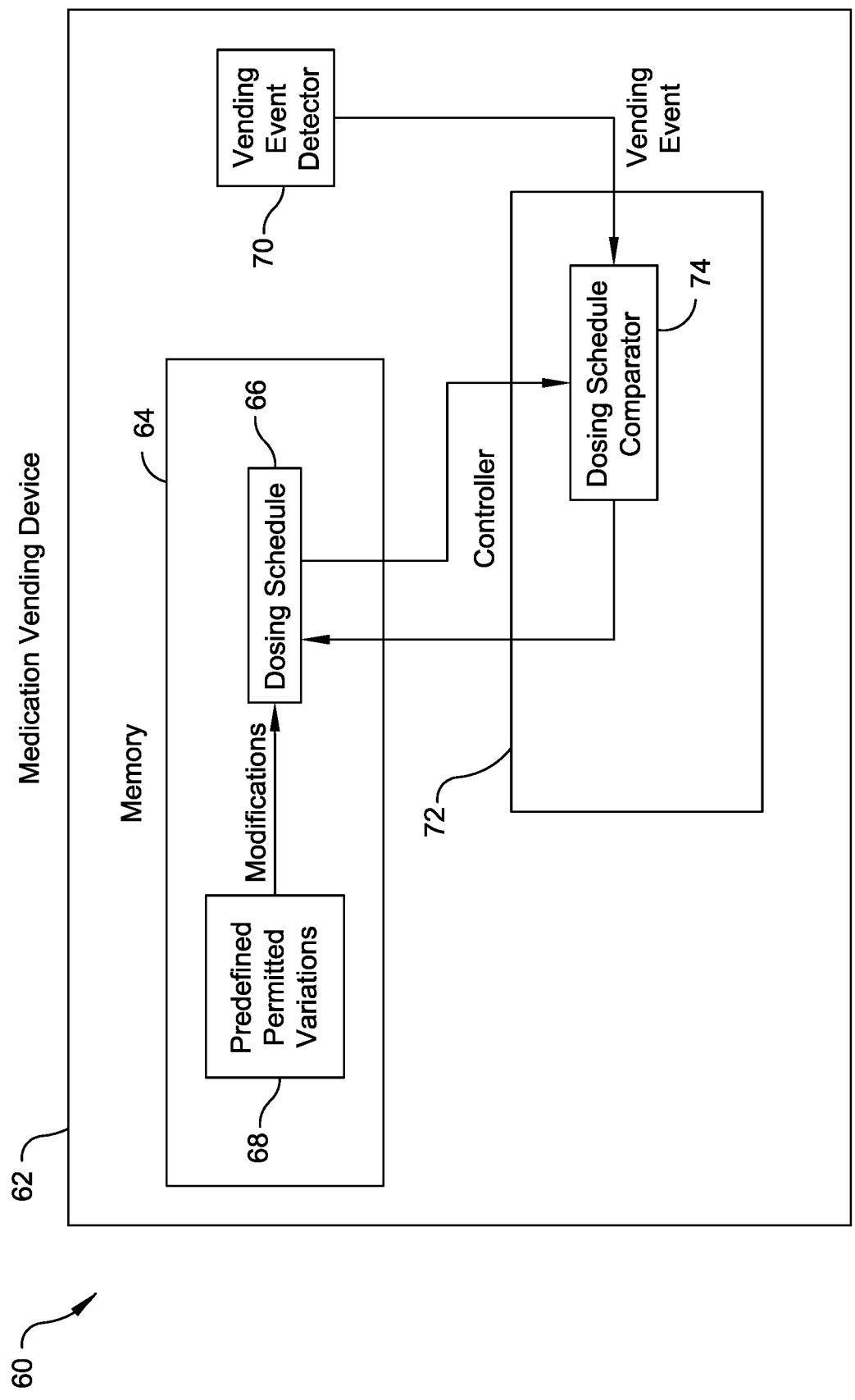
FIG. 6 is a schematic diagram of a system that provides an adaptive dosing schedule for a medication vending device in accordance with another preferred embodiment of the present invention.

FIG. 6 is a schematic diagram of a system 60 that provides adaptive dosing schedules for a medication vending device 62 in accordance with one preferred embodiment of the present invention. One example of the medication vending device 62 may be the device described in U.S. Pat. No. 9,117,010, enhanced with the features described below.

The medication vending device 62 includes memory 64 that stores a dosing schedule 66 for medication loaded into the medical vending device 32. The memory 64 also stores predefined permitted variations 68 to the dosing schedule 66.

The medication vending device 62 also includes a vending event detector 70 that outputs a vending event signal when medication is released from the medication vending device 62.

The medication vending device 62 further includes a controller 72 configured to perform the following functions:
  i. Generate an electronic message whenever a vending event occurs at the medication vending device 62. The medication vending device 62 includes a vending event detector 70 that detects such events.
  ii. Electronically compare the dosing schedule 66 with the vending events in dosing schedule comparator 74, and output signals indicating when the vending events occur outside of the dosing schedule 66.
  iii. Modify the dosing schedule 66 within the predetermined permitted variations based on the output signals.

The dosing schedule 66 may include multiple dosing times per day, as shown in the dosing schedule above. In this instance, the comparison of the dosing schedule 66 with the vending events occurs for each of the dosing times. The dosing schedule 66 may then be modified for one or more of the dosing times within the predefined permitted variations 68 based on the output signals.

In one preferred embodiment, the modification of the dosing schedule 66 occurs only after a consistent pattern of vending events occur outside of the dosing schedule 66, thereby ensuring that any change made to the dosing schedule 66 is not a result of a few outlier vending occurrences.

Example

Initial Dosing Schedule (Same as TABLE 1 Above)
8:00 am
12:00 noon
8:00 pm
The initial dosing schedule may also be referred to as the "default dosing schedule."
Predefined Permitted Variations to the Initial (Default) Dosing Schedule
8:00 am dose: 6:00 am-9:00 am
12:00 noon dose: 12:00 noon-3:00 pm
8:00 pm dose: 7:00 pm-10:00 pm
Sampling Period
7 days (The sampling period would preferably be longer than 7 days, but for ease of illustration, a relatively short sampling period is used.)
Sampling Algorithm and Resultant Dosing Schedule Change
1. Calculate the difference between the average time of vending event for each vended dose (ignoring any missed doses) and the current dosing time.

2. If the difference in time is less than a predefined value (predefined amount of time), such as "less than 20 minutes", do not change the current dosing time.
3. If the difference in time is within a predefined value (predefined amount of time), (e.g., within 10 minutes) of a 30 minute increment, change the dosing time in accordance with the following 30 minute increments shown in TABLE 2:

TABLE 2

| 30 minute increment (in hours) | Dosing schedule change (in hours) |
| --- | --- |
| :30 | :30 |
| 1:00 | 1:00 |
| 1:30 | 1:30 |
| 2:00 | 2:00 |
| 2:30 | 2:30 |
| 3:00 | 3:00 |

The dosing schedule change cannot result in a dosing schedule that is outside of the predefined permitted variations to the dosing schedule. Thus, the changes in TABLE 2 may be constrained by the predefined permitted variations. For example, if the patient has previously had their initial 8:00 am dosing time changed to 9:00 am, and the next sampling period shows that the vending events are occurring on average at 9:30 am, no further upward adjustment is permitted because the initial 8:00 am dosing time can only be varied as late as 9:00 am. However, if the patient has previously had their initial 8:00 am dosing time changed to 9:00 am, and the next sampling period shows that the vending events are occurring on average at 6:00 am, a three hour downward adjustment is permitted because the initial 8:00 am dosing time can be set to be as early as 6:00 am.

FIG. 7 is the first seven-day sampling period after the initial dosing schedule is set. In this example, the sampling algorithm operates as follows:
1. Calculate the difference between the average time of vending event for each vended dose (ignoring any missed doses) and the current dosing time.
2. If the difference is less than 20 minutes, do not change the current dosing time.
3. If the difference is within 10 minutes of a 30 minute increment, change the dosing time in accordance with the increments shown in TABLE 2

Referring to FIG. 7, the initial 8:00 am dosing time had an average time of vending events of 7:45 am. This is less than 20 minutes, so no change is made to the current dosing time. The initial 12:00 noon dosing time had an average time of vending events of 12:25 pm. This is within 10 minutes of a 30 minute increment (12:25 pm is within 10 minutes of 12:30 pm), so the initial 12:00 noon dosing time is changed to 12:30 pm. The initial 8:00 pm dosing time had an average time of vending events of 10:28 pm. This is within 10 minutes of a 30 minute increment (10:28 pm is within 10 minutes of 10:30 pm). However, the initial 8:00 pm dosing time cannot be set any later than 10:00 pm. Accordingly, the initial 8:00 pm dosing time is set to 10:00 pm.

Whenever a change is made to the dosing schedule, the patient is preferably alerted so that they are aware of the new schedule before it replaces the existing dosing schedule. The patient may also be given the opportunity to prevent the new schedule from replacing the existing dosing schedule.

In alternative embodiments, other types of rules may be used. For example, the dosing schedule changes may be limited to one change per three month period, regardless of the changes that would have normally occurred based on the latest sampling of vending times. In another alternative embodiment, a minimum time between doses may be required that will affect the predefined permitted variations. For example, it may be required to always allow for at least 4 hours between doses. In the example above, this means that if the initial 8:00 am dose time was changed to 9:00 am as a result of the process described above, then the 12:00 noon initial dose time will be changed to a 1:00 pm default value, with a new predefined permitted variation between 1:00 pm-3:00 pm.

The sampling algorithm can use other methodologies than the average time of the vending events to minimize outlier vending events. For example, the median time of vending events may be used, or outliers may be ignored when calculating the average or median time. Alternatively, only the most common times of vending events may be used in calculating the time of vending events in the sampling period, especially in scenarios wherein a significant percentage of times of vending events in the sampling period are the same. For example, if during a 7 day sampling period, the initial 8:00 am dose was taken at or close to 8:01 am on 4 of the 7 days, which is immediately after a reminder alert occurs, and was taken at random other times between 6:00 am-10:00 am on the other 3 days, the sampling algorithm would select 8:01 am as the time of the vending event, and no change would be made to the dosing schedule for the 8:00 am dose.

Figure 8:
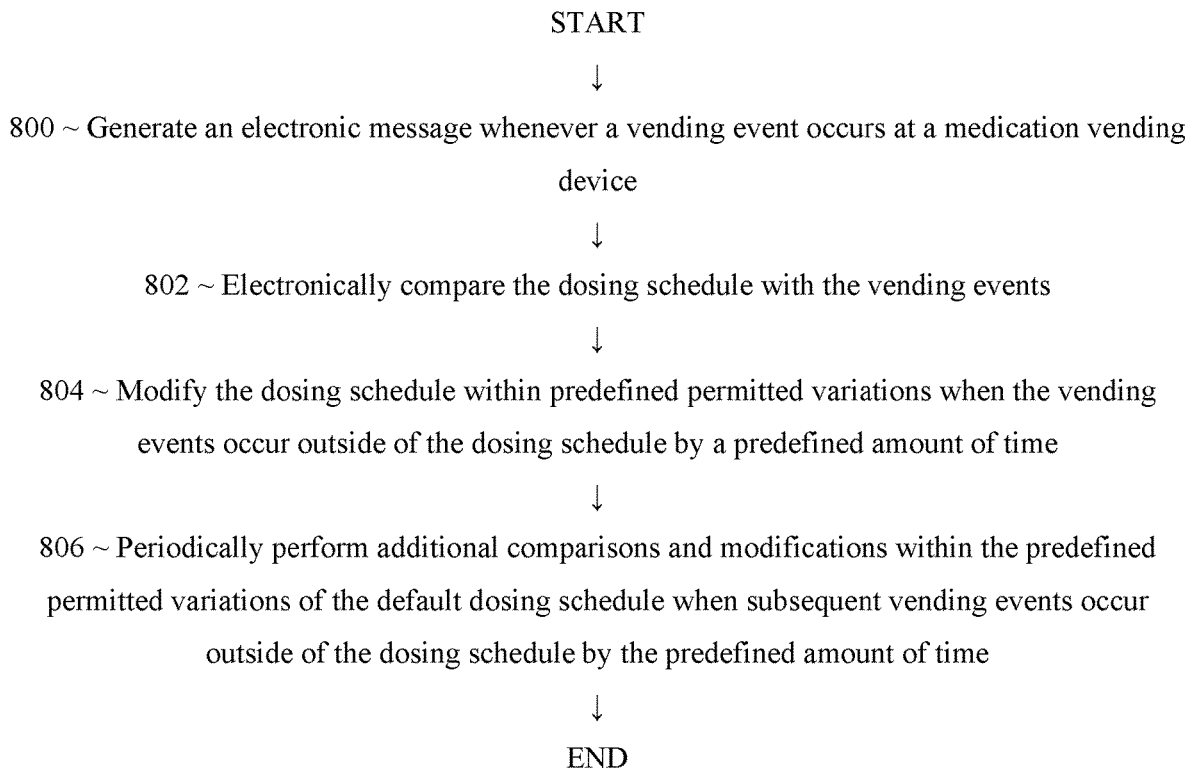
FIG. 8 is a flowchart for implementing the system of FIG. 6.

FIG. 8 is a flowchart for implementing the system 60 of FIG. 6 and includes the following steps.
STEP 800: Generate an electronic message whenever a vending event occurs at a medication vending device.
STEP 802: Electronically compare the dosing schedule with the vending events.
STEP 804: Modify the dosing schedule within predefined permitted variations when the vending events occur outside of the dosing schedule by a predefined amount of time. The modified dosing schedule will be closer to matching times of the vending events.
STEP 806: Periodically perform additional comparisons and modifications within the predefined permitted variations of the default dosing schedule when subsequent vending events occur outside of the dosing schedule by the predefined amount of time. The subsequently modified dosing schedule will be closer to matching times of the most recent vending events.

The present invention may be implemented with any combination of hardware and software. If implemented as a computer-implemented apparatus, the present invention is implemented using means for performing all of the steps and functions described above.

When implemented in software, the software code for the controllers 24, 38 and 72 can be executed on any suitable processor or collection of processors, whether provided in a single computer or distributed among multiple computers.

The present invention can also be included in an article of manufacture (e.g., one or more non-transitory, tangible computer program products) having, for instance, computer readable storage media. The storage media has computer readable program code stored therein that is encoded with instructions for execution by a processor (here, the controllers 24, 38 and 72) for providing and facilitating the mechanisms of the present invention. The article of manufacture can be included as part of a computer system or sold separately.

The storage media can be any known media, such as computer memory, one or more floppy discs, compact discs, optical discs, magnetic tapes, flash memories, circuit configurations in Field Programmable Gate Arrays or other semiconductor devices, or other tangible computer storage medium. The storage media can be transportable, such that the program or programs stored thereon can be loaded onto one or more different computers or other processors to implement various aspects of the present invention as discussed above. The storage media may also be implemented via network storage architecture, wherein many devices, which are paired together, are available to a network.

The computer(s) used herein for the controllers 24, 38 and 72 may be embodied in any of a number of forms, such as a tablet computer. Additionally, a computer may be embedded in a device not generally regarded as a computer but with suitable processing capabilities, including a Personal Digital Assistant (PDA), a smart phone or any other suitable portable, mobile, or fixed electronic device.

The controllers 24, 38 and 72 are not a general-purpose computers, but instead are specialized computer machines that perform a myriad of functions (e.g., integration with a medical diagnostics device, compliance monitoring, dosing schedule modifications) that are not native to a general-purpose computer, absent the addition of specialized programming.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

The terms "program" or "software" are used herein in a generic sense to refer to any type of computer code or set of computer-executable instructions that can be employed to program a computer or other processor to implement various aspects of the present invention as discussed above. The computer program need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, and the like, that perform particular tasks or implement particular abstract data types. The functionality of the program modules may be combined or distributed as desired in various embodiments.

Data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags, or other mechanisms that establish relationship between data elements.

Preferred embodiments of the present invention may be implemented as methods, of which examples have been provided. The acts performed as part of the methods may be ordered in any suitable way. Accordingly, embodiments may be constructed in which acts are performed in an order different than illustrated, which may include performing some acts simultaneously, even though such acts are shown as being sequentially performed in illustrative embodiments.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention.

What is claimed is:

1. A medication vending device associated with a patient, the medication vending device comprising:
    (a) an input interface configured to receive a first signal outputted by a medical diagnostics device, the first signal indicating a parameter of the patient's body, the input interface including decoding logic to extract the parameter of the patient's body from the first signal;
    (b) a memory that stores:
        (i) a dosing schedule for medication loaded into the device, and
        (ii) a predefined parameter range for the parameter received from the medical diagnostics device that is designated as being normal for the patient, wherein a parameter that is outside of the predefined range is designated as being abnormal for the patient; and
    (c) a controller configured to:
        (i) generate an electronic message whenever a vending event occurs at the medication vending device,
        (ii) electronically compare the dosing schedule with the vending events, and output a second signal indicating when the medication is being properly vended in accordance with the dosing schedule, thereby indicating that the patient is adhering to the dosing schedule,
        (iii) electronically compare the parameter received from the medical diagnostics device to the predefined parameter range, and output a third signal when the parameter is abnormal for the patient, and
        (iv) generate an alert signal when the controller outputs both the second signal and the third signal, thereby indicating that the patient is adhering to the dosing schedule, but that the parameter is abnormal for the patient.

2. The device of claim 1 further comprising:
    (d) a user interface device including a display, and
    wherein the controller further configured to:
        (v) display the alert signal on the display, the alert signal informing the patient to contact a medical provider regarding the abnormal parameter.

3. The device of claim 1 further comprising:
    (d) a communication module configured to communicate electronic messages from the device to an external location, and
    wherein the controller is further configured to:
        (v) electronically communicate the alert signal to the external location via the communication module, the alert signal indicating the presence of the abnormal parameter.

4. A method of using a medication vending device associated with a patient, the medication vending device including (i) a controller, (ii) a vending event detector, (iii) an input interface including decoding logic, and (iv) a memory that stores (A) a dosing schedule for medication loaded into the device, and (B) a predefined parameter range for a parameter received from a medical diagnostics device that is designated as being normal for the patient, wherein a parameter that is outside of the predefined range is designated as being abnormal for the patient, the method comprising:
- (a) receiving at the input interface a first signal outputted by the medical diagnostics device, the first signal indicating a parameter of the patient's body;
- (b) extracting the parameter of the patient's body from the first signal using the decoding logic of the input interface;
- (c) generating an electronic message, using the vending event detector, whenever a vending event occurs at the medication vending device;
- (d) electronically comparing, using the controller, the dosing schedule with the vending events, and outputting a second signal indicating when the medication is being properly vended in accordance with the dosing schedule, thereby indicating that the patient is adhering to the dosing schedule;
- (e) electronically comparing, using the controller, the parameter received from the medical diagnostics device to the predefined parameter range, and outputting a third signal when the parameter is abnormal for the patient; and
- (f) generating an alert signal when the controller outputs both the second signal and the third signal, thereby indicating that the patient is adhering to the dosing schedule, but that the parameter is abnormal for the patient.

5. The method of claim 4 wherein the medication vending device further includes a user interface device including a display, the method further comprising:
- (g) displaying the alert signal on the display, the alert signal informing the patient to contact a medical provider regarding the abnormal parameter.

6. The method of claim 4 wherein the medication vending device further includes a communication module configured to communicate electronic messages from the device to an external location, the method further comprising:
- (g) electronically communicating the alert signal to the external location via the communication module, the alert signal indicating the presence of the abnormal parameter.

* * * * *